United States Patent [19]
Nimberger et al.

[11] Patent Number: 5,109,712
[45] Date of Patent: May 5, 1992

[54] PORTABLE SAMPLE CYLINDER WITH REDUCED SEAL PERMEABILITY

[75] Inventors: Spencer M. Nimberger, Houston; Robert L. Ward, Missouri City, both of Tex.

[73] Assignee: Precision General, Inc., Houston, Tex.

[21] Appl. No.: 586,544

[22] Filed: Sep. 21, 1990

[51] Int. Cl.$^5$ ............................................. G01N 1/12
[52] U.S. Cl. ............................ 73/864.62; 277/169; 220/378
[58] Field of Search ............... 73/864.62, 864.91; 220/228, 378; 215/234, 341, 352; 277/2, 169

[56] References Cited

U.S. PATENT DOCUMENTS

| | | | |
|---|---|---|---|
| 984,808 | 2/1911 | Glocker | 215/352 |
| 1,629,022 | 5/1927 | Davis et al. | 220/378 |
| 2,376,593 | 5/1945 | Hellen | 220/378 |
| 2,467,061 | 4/1949 | Mason | 220/378 |
| 2,528,665 | 11/1950 | Peterson et al. | 220/378 |
| 2,663,268 | 12/1953 | Ahnell | 220/378 |
| 3,214,181 | 10/1965 | Rood | 220/378 |
| 3,289,879 | 12/1966 | Williams | 220/378 |
| 3,782,587 | 1/1974 | Brothers | 220/378 |
| 3,892,130 | 7/1975 | Winget et al. | 73/864.62 |
| 4,108,327 | 8/1978 | Shonerd et al. | 220/378 |
| 4,418,830 | 12/1983 | Dzung et al. | 220/378 |
| 4,459,865 | 7/1984 | Welder | 73/864.62 |
| 4,862,754 | 9/1989 | Nimberger | 73/864.62 |
| 4,936,483 | 6/1990 | Ballu | 220/378 |

FOREIGN PATENT DOCUMENTS

| | | | |
|---|---|---|---|
| 1023678 | 3/1953 | France | 220/378 |
| 1166642 | 11/1958 | France | 220/378 |

OTHER PUBLICATIONS

Advertisement: "Free Piston Product Vessel LPR-2" by Y-Z Industries, Inc. (Nov. 24, 1986).

*Primary Examiner*—Robert Raevis
*Attorney, Agent, or Firm*—Kirk & Lindsay

[57] ABSTRACT

A portable sample cylinder assembly is provided for transporting a fluid. The sample cylinder assembly includes a housing defining in part an internal fluid chamber, a first end cap at one end of the housing, and a second end cap at an opposing end of the housing. At least one of the end caps includes a stop surface and an annular groove. An elastomeric seal is positioned within the groove for static sealing between the end cap and the housing. The end of the housing includes an end surface for metal-to-metal engagement with the stop surface, and a compressional surface for applying a compressional force to the elastomeric seal in response to axial movement of the end surface toward the stop surface. A plurality of connector rods may be used to controllably move the end cap axially toward the housing and thereby compress the elastomeric seal to reduce the permeability of the seal. The elastomeric seal preferably has a circular cross-sectional configuration prior to compressional force being applied to the seal, and a base portion of the groove opposite the compressional surface with respect to the elastomeric seal as a semi-circular cross-sectional configuration.

20 Claims, 1 Drawing Sheet

PORTABLE SAMPLE CYLINDER WITH REDUCED SEAL PERMEABILITY

BACKGROUND OF THE INVENTION

1. Field of the Invention

The present invention relates to fluid containers having elastomeric seals between enclosure components and, more particularly, relates to an improved portable piston style sample cylinder having reduced seal permeability to pressurized fluid within the sample cylinder.

2. Description of the Background

Portable sample cylinders for collecting and transporting fluid samples have long been used in the liquid petroleum gases (LPG) industry. Such sample cylinders commonly include a piston movable within the cylinder, which allows the fluids to be collected and transported at the pressure of the fluids when sampled, so that the physical state of the fluid is not altered. Since the sampled fluid is the basis for subsequent tests to determine the constituents or caloric content of the fluid, care must be taken that no constituents of the sample leak from the sample chamber. Moreover, conventional seal lubricants tend to absorb certain chemical groups within the LPG or other sampled fluid, and thus are generally avoided. A representative portable piston sampler and background relating to such samplers is disclosed in U.S. Pat. 4,862,754, hereby incorporated by reference.

Problems with respect to the integrity of the fluid are heightened when the sample cylinder as shown in the '754 patent is used to transmit "speciality gases." Speciality gases are extremely expensive since the constituents of the fluid are carefully controlled. Such gases are commonly used as a standard to verify the accuracy or to calibrate precision test equipment, such as chromatographic equipment. Moreover, such speciality gases frequently employ constituents having very small molecules, and these molecules tend to escape from the container at substantially different rates than larger molecules constituents. If the vapor pressure of the "high end" gas is 800 PSI at room temperature, the speciality gas is typically maintained at a slightly higher pressure, e.g. 850 PSI, to prevent vaporization. A pressurized gas may be housed within the sample cylinder separate from the speciality gas, and the piston within the cylinder separates these fluids while maintaining the speciality gas within its desired pressure range.

A further problem with sample cylinders used to transmit LPG and other fluids, and particularly for those vessels used to transmit speciality gases, is the permeability of the seals used to seal container components. Since some of the sample constituents chemically react with most if not all elastomeric seal materials differently than other sample constituents, and since some constituents are more easily absorbed into the elastomeric seal material than other constituents, the permeability of the seal can have a significant effect on the integrity of the fluid in the cylinder. The integrity of a small quantity of speciality gas costing thousands of dollars can be destroyed by an elastomeric seal which (a) allows some portion of the pressurized fluid to escape from the container, (b) chemically reacts with some constituent of the fluid, or (c) alters the composition of the sample by allowing one or more constituents to become absorbed into the seal material.

The disadvantages of the prior art are overcome by the present invention, and an improved portable sample cylinder with reduced seal permeability is hereinafter disclosed for maintaining the integrity of the sampled fluid. Also disclosed is an improved method to manufacture a sample cylinder to achieve the benefit of reduced seal permeability.

SUMMARY OF THE INVENTION

In a preferred embodiment, a portable sample cylinder comprises an elongate monolithic cylinder and a pair of end plates each at a respective end of the cylinder. Elongate rods are perferrably used to interconnect the end plates, thereby fixing the cylinder between the end plates. A sample chamber within the cylinder houses the sample fluid at greater than atmospheric pressure. The pressurized fluid may be stored and transported to a test site to determine its properties, or may be a fluid such as a speciality gas with predetermined properties used to verify test equipment.

According to the present invention, each of the end plates may include a circular groove for receiving an elastomeric seal, which forms a static seal between the metallic end plate and the metallic cylinder. An end surface of the cylinder is adapted for metal-to-metal engagement with a stop surface of the end plate, thereby limiting the axial movement of these components toward each other. A compressional surface on the cylinder is adapted to compress the elastomeric seal as the end surface of the cylinder moves toward engagement with the stop surface. The cross sectional geometry of the groove will depend on the configuration of the end of the cylinder, although a base portion of the groove opposite the compressional surface on the cylinder preferably has a cross-sectional configuration corresponding to the configuration of that portion of the elastomeric seal which fills this void. Prior to assembly, the seal may have a circular cross-sectional configuration, in which case the base portion of the groove has a semicircular configuration.

The seal is mechanically compressed as the threaded rods are tightened, thereby bringing the end plates closer together with the cylinder sandwiched therebetween. Tightening of the rods will continue until the end surfaces of the cylinder engage the respective stop surfaces on the end plates. Since the seal is substantially compressed, the amount of compression is predetermined by the position of the end surface with respect to stop surface, and the compression of the seal is substantially uniform, permeability of the seal is substantially reduced. Various materials may be used as the elastomeric seal material, depending upon the characteristics of the fluid to be transported within the cylinder.

It is an object of the present invention to provide an improved sample vessel with reduced seal permeability to maintain the integrity of a pressurized fluid within the vessel.

Another object of the invention is to provide a low cost and highly reliable sample vessel for collecting and/or transporting fluids without altering the composition of the fluid constituents.

It is a feature of the present invention that a static seal between a cylinder and an end plate is housed within a groove having a base portion with a geometry corresponding to that portion of the seal which fills this void.

It is another feature of this invention that the end surface of the cylinder is adapted for engagement with a stop surface on an end plate, and that a compressional surface on the cylinder engages and compresses the seal as the cylinder moves axially toward engagement with the end surface without pinching the seal.

It is an advantage of the present invention that a low-cost seal having a circular cross-sectional configuration may be used, in which case the base portion of the groove has a generally semi-cylindrical configuration.

It is a further advantage of this invention that the elastomeric seal may be formed from various materials, depending on the composition of the fluid to be stored within the vessel.

These and further objects, features, and advantages of the present invention will become apparent from the following detailed description, wherein reference is made to the figures in accompanying drawings.

BRIEF DESCRIPTIONS OF THE DRAWINGS

DETAILED DESCRIPTION OF PREFERRED EMBODIMENTS

Figure 1:
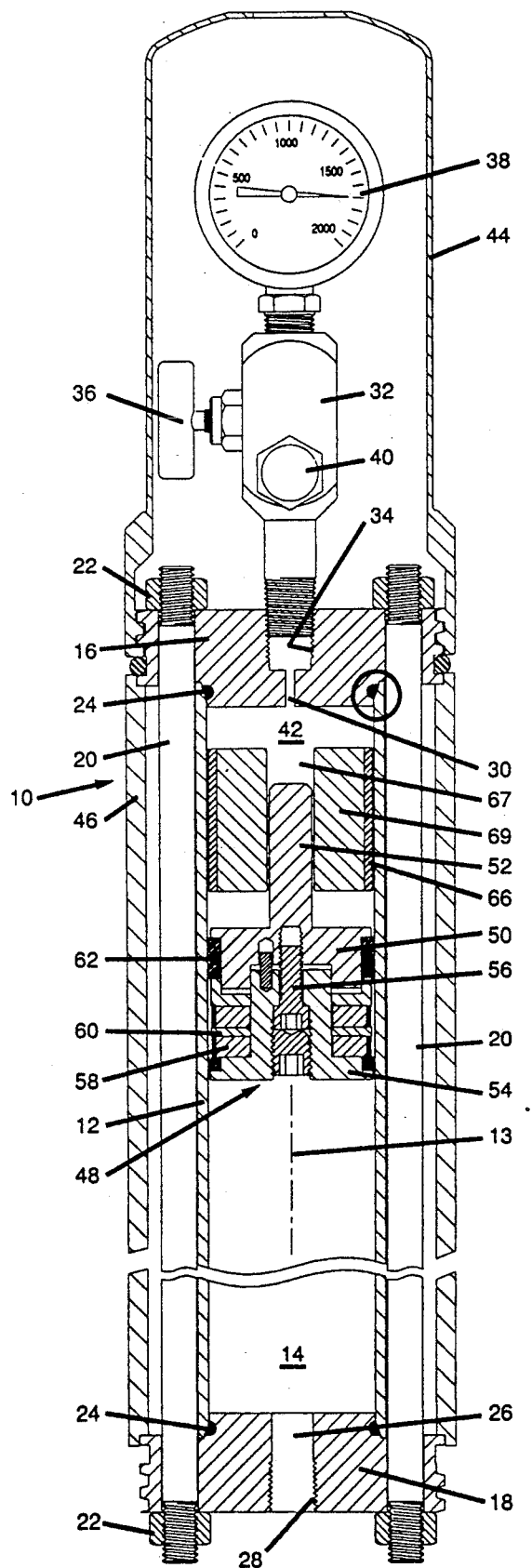
FIG. 1 is a simplified pictorial view, partially in cross-section, of a sample cylinder according to the present invention.

FIG. 1 generally depicts one embodiment of the portable sample cylinder or vessel 10 according to the present invention. The sample cylinder 10 includes an elongate, preferably monolithic metallic sleeve or cylinder 12 having a central axis 13 and in part defining the sample fluid chamber 42. The pair of similar end caps 16, 18 are provided at opposing ends of the cylinder 12, and each end cap includes a plurality of apertures for receiving respective threaded rods 20. The nuts 22 cooperate with the rods 20 to sandwich the cylinder 12 between the end caps. The rods 20 are preferably spaced circumferentially about the axis 13 and radially outward from the cylinder 12. A pair of O-rings 24 statically seal each end cap with the cylinder 12, and are discussed in detail below.

End cap 18 includes through inlet port 26 for transmitting fluid into the chamber 14 from a larger container, such as a flow line, tank, etc., and the end cap 18 is preferably provided with an NPT thread 28 for sealing with a suitable flow line connection (not shown). End cap 16 includes a similar through passage 30, and valve manifold 32 is shown threadably secured to its corresponding NPT threads 34. Valve 36 may be open to allow fluid pressure within the cylinder 12 to be transmitted to a pressure sensor, guage, monitor or similar device 38. Valve 36 may be selectively opened to introduce a selected gas into chamber 42 within the cylinder 12, then closed to seal the gas within the cylinder. Once chamber 42 has been pressurized, the valve 40 may remain closed. Protective enclosure 44 may be threadably secured to the end caps 16 to shield the manifold 32 and guage and to minimize the safety risks associated with transporting highly pressurized fluids. An outer sleeve-like protective case 46 may also be secured to the end caps to enclose the threaded rods 20 positioned in the annulus between 46 and 12.

An axially moveable piston assembly 48 may be provided within the cylinder 12 for sealing therewith and separating fluid chamber 42 from charge chamber 14. The piston assembly will thus maintain pressure in chamber 42 identical to pressure in chamber 14, yet isolate sensor 38 from the fluid in chamber 14. The assembly 48 includes a piston body 50 having a projection 52 at one end thereof. Tightening of the bolt 56 axially compresses one or more O-ring seals 62 provided for sealing between the body 50 and cylinder 12 and moves the end cap 54 and plate 60 toward the body 50. A mixer element 69 is provided within the chamber 14, and includes an outer plastic ring 66 and a aperture 67 for receiving the projection 52. The piston assembly and mixer element briefly described above may be identical to the assembly and mixing element disclosed in U.S. Pat. No. 4,862,754, and further details regarding these components are hereby incorporated by reference.

Figure 2:
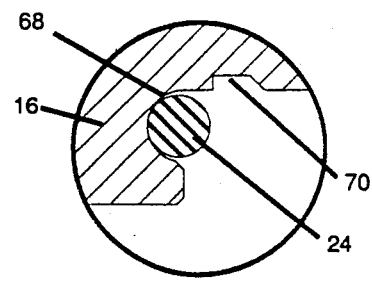
FIG. 2 is a detailed cross-section view a portion of an end plate and one embodiment of a seal prior to securing the cylinder between the end plates.

The configuration of the annular groove in each end cap, the configuration of the seal in each annular groove, and the configuration of the end of the cylinder which engages each end cap may be identical, and thus only one end cap 16 and the end 64 of the cylinder 12 are described in detail below. Referring to FIG. 2, the groove 68 in end cap 16 is formed for receiving a low-cost seal 24 having a circular cross-sectional configuration, and at least the base portion of the groove has a substantially similar semi-cross-sectional configuration. Also, the end cap 16 is formed to include annular stop surface 70 for metal-to-metal engagement with the end 64 of the cylinder 12.

Figure 3:
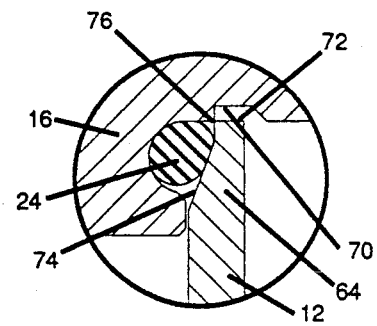
FIG. 3 is a detailed cross-sectional view of the apparatus shown in FIG. 1, with the end of the cylinder in contact with the seal but out of metal-to-metal engagement with the end plate.
Figure 4:
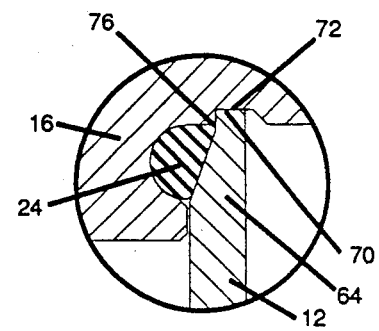
FIG. 4 is a detailed cross-sectional view of the apparatus shown in FIGS. 2 and 3 in an assembled position, with the cylinder end surface in metal-to-metal engagement with the end plate.

Referring to FIG. 3, the end 64 of the cylinder tube 12 includes an end surface 72 adapted for planar engagement with the stop surface 70, and a compressional surface 74 for contacting the seal 24 and both compressing and deforming the seal 24 as the end 64 moves axially toward the end cap 16. The end surface 72 is perpendicular to axis 13 of the cylinder 12, and the compressional surface has a frustroconical configuration with its imaginery apex along the axis 13 and spaced opposite NPT threads 34 with respect to the passageway 30. As the surface 72 approaches the surface 70, the surface 74 begins to compress the seal 24. Before the seal is fully compressed, however, the surface 72 passes by the corner 76, so that continued movement will not allow the seal 24 to flow into the cavity between the surface 70 and corner 76. As shown in FIG. 4, the surface 72 is in metal-to-metal engagement with the surface 70, thereby further compressing the seal 24 to substantially reduce its permeability to fluids within the cylinder tube 12. The end surface and stop surface thus cooperate to limit the axial movement of the cylinder toward the end cap, and thereby control the extent of compression of the elastomeric seal 24. Preferably, at least a base portion of the groove 68 has a cross-sectional configuration substantially equivalent to the configuration of at least that portion of the seal which will occupy the void in the base portion of the groove. This feature desireably allows the seal to be more uniformly compressed, and also allows high seal compressibility with a relatively short axial travel of the surface 72 toward the surface 70.

Low permeability for the seal with the end cap 18 is not essential, since the sample fluid would not engage this seal. Although a sample cylinder as described herein includes a piston to seperate the cylinder into two chambers, a simple storage cylinder need not contain a piston. If the piston assembly or other fluid separation means is not used, the entire fluid chamber 14 within the housing 12 would be filled by the sample fluid (or speciality gas), and thus chamber 14 would be essentially defined by the cylinder 12 and the end caps 16, 18. Even if the piston assembly is not utilized, the seals with both end caps are preferably formed in accordance with the concept of the present invention to reduce permeability. Although not shown in FIG. 1, it should be understood that the groove in the end cap for the seals 24 may have a cross-sectional configuration other than circular, and that the effective cross-sectional configuration of the groove may be altered by adding metal inserts in the formed groove. For example, if the cross-sectional configuration of the groove in the piston assembly 48 is rectangular, an annular ring with a rectangular-shaped base and a semi-circular shaped top could be fitted in the groove, so that the elastomeric seal with a circular cross-sectional configuration engaged the semi-circular surface of the ring.

Figure 5:
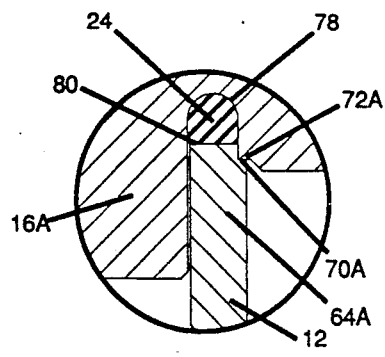
FIG. 5 is a detailed cross-sectional view of an alternate embodiment of the apparatus shown in FIG. 4.

FIG. 5 depicts an alternate embodiment illustrating a groove 78 in the end cap 16A, the groove 78 again having a base portion with a semi-circular cross-sectional configuration for receiving the elastomeric seal 24. Prior to assembly, the seal 24 may have a circular cross-sectional configuration, as generally shown in FIG. 2. In FIG. 5, the stop surface 70A on the end plate 16 is shown in metal-to-metal engagement with the end surface 72A on the end 64A of the cylindrical tube 12. Both surfaces 70A and 72A are planar surfaces each perpendicular to the axis 13 of the tube 12. The compressional surface 80 on the end 64A is also perpendicular to the axis 13, and exerts an axially-directed force on the seal 24 to compress the seal 24 and thus reduce its permeability. Again, the position of the surface 80 with respect to the surface 72A is carefully controlled to limit the compression of the seal 24, since further compression will be prohibited once the end surface 72A engages the stop surface 70A. The previously described embodiment is preferred, however, since the compressed seal as shown in FIG. 4 provides a longer path of sealing to leakage of fluid than the compressed seal of FIG. 5. Also, the taper surface 74 provides increased seal compressive force for the same axially compressive force on the rods 20 than the end surface 80 as shown in FIG. 5.

According to the method of the present invention, the portable sampling cylinder is generally manufactured and assembled according to conventional techniques, and only the differences in manufacturing and assembling are discussed herein. A stop surface and an annular groove are formed in each of the end caps, as described above. Also, each end of the cylinder tube 12 is formed with an end surface for engagement with the stop surface to limit axial movement of the cylinder tube with respect to the end cap, and also with a compressional surface for applying a compressional force to the elastomeric seal in response to axial movement of the end surface toward the stop surface. Preferably at least a base portion of the annular groove opposite the compressional surface in respect to the elastomeric seal is formed to have a cross-sectional configuration substantially equivalent to the cross-sectional configuration of that portion of the elastomeric seal which will be positioned within the base portion prior to applying the compressional force to the elastomeric seal. The piston assembly and mixing element may or may not be housed within the tube 12.

With the seals 24 in each of the annular grooves within the end cap 16, 18, the nuts 22 may be uniformly tightened to move the first and second end caps axially toward the cylinder tube 12, respectively, and thereby compress the elastomeric seals and reduce the permeability of the seals. The operator will be able to easily determine when rotation of the nuts 22 and thus axial movement of the end plates with respect to the cylinder 12 should be terminated, since substantially increased torque will be required for further rotation once the end surfaces engage the planar stop surfaces.

The rods 20 and the nuts 22 provide an easy, low cost, and reliable technique to axially move each of the end caps toward the cylinder, although various other conventional connection means may be used to bring these components axially together. The significant advantage of the threaded rod design is that the sample cylinder may be easily disassembled to remove or repair a piston or assembly, the mixing element, or the seals 24. The term "elastomeric" as used herein is intended to encompass the terms plastic, thermoplastic, and similar terms indicative of high elasticity, and includes material such as nylon, Delrin, polytetraflurothylene, and PEEK. The selected material for the elastomeric seals will depend upon the characteristics of the fluid to be sealed within the sample cylinder. The term "fluid" as used herein should be understood to include gases, liquids, and mixtures of gases and liquids under various pressures.

Although the invention has been described in terms of specified embodiments which are set forth in detail, it should be understood that this is by illustration only, and that the invention is not limited thereto, since other alternative embodiments and manufacturing methods will become apparent to those skilled in the art in view of this disclosure. Accordingly, modifications are contemplated which can be made without departing the spirit of the described invention, whose scope is determined by the claims attached hereto.

What is claimed is:

1. A portable sample cylinder for transporting a fluid sample, the sample cylinder including a cylindrical tube housing a sample chamber and defining a sample cylinder axis, an end cap at one end of the tube, and a piston slidabley movable within the sample chamber in sealing relationship with the sample cylinder, the portable sample cylinder further comprising:

the end cap including a planar stop surface an annular grove and a corner positioned between the stop surface and the annular grove;

an elastomeric seal positioned within the annular groove for static sealing between the end cap and the cylindrical tube;

the end of the cylindrical tube including (a) a planar end surface for engagement with the stop surface to limit axial movement of the cylindrical tube with respect to the end cap, and (b) a frustoconical compressional surface for applying a compressional force to the elastomeric seal in response to axial movement of the end surface toward the stop surface; and connector means for moving the end cap axially to secure the cylindrical tube to the end cap and thereby compress the elastomeric seal to reduce the permeability of the elastomeric seal.

2. The portable sample cylinder as defined in claim 1, further comprising:

the annular groove having a base portion opposite the compressional surface with respect to the elastomeric seal, the base portion having a cross-sectional configuration substantially equivalent to the cross-sectional configuration of a portion of the elastomeric seal positioned within the base portion prior to the compressional surface applying the compressional force to the elastomeric seal.

3. The portable sample cylinder as defined in claim 2, wherein:

the elastomeric seal has a substantially circular cross-sectional configuration prior to the compressional surface applying the compressional forces to the elastomeric seal; and the base portion of the groove has a semi-circular cross-sectional configuration.

4. The portable sample cylinder as defined in claim 1, further comprising:

a second end cap including a second stop surface and a second annular groove;

a second elastomeric seal positioned within the second annular groove for sealing engagement between the second end cap and the cylindrical tube; and the second end of the cylindrical tube including (a) a second end surface for engagement with the second stop surface to limit axial movement of the cylindrical tube with respect to the second end cap, and (b) a second compressional surface for applying a compressional force to the second elastomeric seal in response to axial movement of the second end surface toward the second stop surface.

5. The portable sample cylinder as defined in claim 4, wherein:

one of the first and second end caps includes a sample inlet port through the one end cap for transmitting fluid into the sample chamber; and the other of the first or second end caps including a fluid passageway therethrough.

6. The portable sample cylinder as defined in claim 1, wherein the connector means comprises:

a plurality of threaded rods each positioned radially outward of the cylindrical tube for removeably interconnecting the end cap.

7. The portable sample cylinder as defined in claim 1, further comprising:

a mixing element positioned within the sample chamber.

8. The portable sample cylinder as defined in claim 7, within the piston assembly further comprises:

an elastomeric piston seal for sealing between a piston body and the cylindrical tube; and mechanical pressure application means for applying a mechanical compressive force to the elastomeric piston seal to reduce the permeability of the elastomeric piston seal.

9. The portable sample cylinder as defined in claim 1, wherein the cylinder tube further includes a corner having an inner diameter substantially equivalent to an outer diameter of the corner of the end cap, and wherein the frustoconical compressional surface has one end having an inner diameter substantially equivalent to an outer diameter of the corner of the end cap and another end having an inner diameter substantially equivalent to an outer diameter of a leading end of the end cap.

10. A portable vessel for transporting a fluid, the vessel including a housing defining in part an internal fluid chamber and a vessel axis, an end cap at one end of the housing, the portable vessel further comprising:

the end cap including a planar stop surface an annular groove and a corner positioned between the stop surface and the annular groove;

an elastomeric seal positioned within the annular groove for static sealing between the end cap and the housing;

the end of the housing including (a) a planar end surface for engagement with the stop surface to limit axial movement of the housing with respect to the end cap, and (b) a frustoconical compressional surface for applying a compressional force to the elastomeric seal in response to axial movement of the end surface toward the stop surface; and connector means for controllably moving the end cap axially toward the housing and thereby compress the elastomeric seal to reduce the permeability of the elastomeric seal.

11. The portable vessel as defined in claim 10, further comprising:

the annular groove having a base portion opposite the compressional surface with respect to the elastomeric seal, the base portion having a cross-sectional configuration substantially equivalent to the cross-sectional configuration of a portion of the elastomeric seal positioned within the base portion prior to the compressional surface applying the compressional force to the elastomeric seal.

12. The portable vessel as defined in claim 11, wherein:

the elastomeric seal has a substantially circular cross-sectional configuration prior to the compressional surface applying the compressional forces to the elastomeric seal; and the base portion of the groove has a semi-circular cross-sectional configuration.

13. The portable vessel as defined in claim 10, further comprising:

a second end cap including a second stop surface and a second annular groove;

a second elastomeric seal positioned within the second annular groove for sealing engagement between the second end cap and the housing; and the second end of the housing including (a) a second end surface for engagement with the second stop surface to limit axial movement of the housing with respect to the second end cap, and (b) a second compressional surface for applying a compressional force to the second elastomeric seal in response to axial movement of the second end surface toward the second stop surface.

14. The portable vessel as defined in claim 13, wherein:

one of the first or second end caps includes a sample inlet port through the one end cap for transmitting fluid into the sample chamber; and the other of the first or second end caps including a fluid passageway therethrough.

15. The portable vessel as defined in claim 10, wherein the connector means comprises:

a plurality of rods each positioned radially outward of the housing for removeably interconnecting the end cap.

16. The portable vessel as defined in claim 10, further comprising:
   a piston assembly sealingly movable within the housing for separating the sample chamber from a charge chamber; and
   the piston assembly includes (a) an elastomeric piston seal for sealing between a piston body and the housing, and (b) mechanical pressure application means for applying a mechanical compressive force to the elastomeric piston seal to reduce the permeability of the elastomeric piston seal.

17. The portable sample cylinder as defined in claim 10, wherein the housing further includes a corner having an inner diameter substantially equivalent to an outer diameter of the corner of the end cap, and wherein the frustoconical compressional surface has one end having an inner diameter substantially equivalent to an outer diameter of the corner of the end cap and another end having an inner diameter substantially equivalent to an outer diameter of a leading end of the end cap.

18. A method of manufacturing a vessel for transporting a fluid sample, the vessel including a cylindrical tube housing a sample chamber and defining a sample cylinder axis, an end cap at one end of the tube, and a first elastomeric seal for sealing engagement between the cylindrical tube and the end cap, the method comprising:
   forming a planar stop surface, an annular grove, and a corner positioned between the stop surface and the annular groove on the end cap;
   forming a planar end surface on the end of the cylindrical tube;
   forming a frustoconical compressional surface on the end of the cylindrical tube;
   positioning the elastomeric seal within the annular groove; and
   moving the end cap axially toward the cylindrical tube thereby compressing the elastomeric seal by the compressional surface to reduce the permeability of the elastomeric seal.

19. The method as defined in claim 18, further comprising:
   forming the annular groove with a base portion opposite the compressional surface with respect to the elastomeric seal, the base portion having a cross-sectional configuration substantially equivalent to the cross-sectional configuration of a portion of the elastomeric seal positioned within the base portion prior to applying the compressional force to the elastomeric seal.

20. The method as defined in claim 19, further comprising:
   selecting an elastomeric seal with a substantially circular cross-sectional configuration prior to applying the compressional force to the first elastomeric seal; and
   forming the base portion of the groove with a semicircular cross-sectional configuration.

* * * * *